(12) United States Patent
Gervais

(10) Patent No.: US 6,340,695 B1
(45) Date of Patent: Jan. 22, 2002

(54) RAPID ONSET FORMULATION

(75) Inventor: Eric Gervais, Laval (CA)

(73) Assignee: Duchesnay Inc., Laval (CA)

( * ) Notice: Subject to any disclaimer, the term of this patent is extended or adjusted under 35 U.S.C. 154(b) by 0 days.

(21) Appl. No.: 09/885,051

(22) Filed: Jun. 21, 2001

(51) Int. Cl.⁷ .............................................. A61K 31/44
(52) U.S. Cl. ...................................... 514/345; 514/357
(58) Field of Search .................................. 514/345, 357

(56) References Cited

U.S. PATENT DOCUMENTS 6,013,280 A * 1/2000 Frisbee et al. .............. 424/464

FOREIGN PATENT DOCUMENTS

CA          2139896    * 11/1996

* cited by examiner

Primary Examiner—Raymond Henley, III
(74) Attorney, Agent, or Firm—Goudreau Gage Dubuc

(57) ABSTRACT

Provided herein is a novel enterically-coated pyridoxine HCl and doxylamine succinate rapid onset formulation comprising a disintegrating agent such that the following dissolution profiles are satisfied when measured in 1000 ml phosphate buffer at pH 6.8 and 37° C. in a type 2 dissolution apparatus at 100 rpm:

(a) at least about 40% of the total pyridoxine HCl and doxylamine succinate is dissolved after 30 minutes of measurement;

(b) at least about 70% of the total pyridoxine HCl and doxylamine succinate is dissolved after 60 minutes of measurement;

(c) at least about 80% of the total pyridoxine HCl and doxylamine succinate is dissolved after 90 minutes of measurement;

(d) at about 90% of the total pyridoxine HCl and doxylamine succinate is dissolved after 120 minutes of measurement.

Preferably the formulation will contain a core coated with at least one enteric coating, the core comprising pyridoxine HCl, doxylamine succinate and the following non-active excipients: a filler or binder, a disintegrating agent, a lubricant, a silica flow conditioner and a stabilizing agent.

30 Claims, 2 Drawing Sheets

RAPID ONSET FORMULATION

BACKGROUND OF THE INVENTION

1. Field of the Invention

The present invention relates to a rapid onset formulation, preferably in form of an enterically coated tablet, for a medicament comprising a synergistic duo of active ingredients namely, doxylamine succinate and pyridoxine HCl, hereinafter referred to as "DS-P". DS-P is useful in the treatment of nausea and vomiting, especially, but not limited to, during pregnancy, hereinafter referred to as "NVP". Thus the present invention is concerned with all known and future therapeutic indications of DS-P.

2. The Prior Art

Pharmaceutical formulations of DS-P are known. The current formulation, commercially available in Canada under the name Diclectin (Duchesnay Inc.) comprises the following active ingredients: pyridoxine HCl and Doxylamine succinate. It additionally comprises the following excipients: lactose, microcrystalline cellulose, magnesium trisilicate, silicon dioxide and magnesium stearate.

Diclectin is the world's most studied drug in regard to its safety during pregnancy. Because of its excellent safety profile, Diclectin is the drug of choice for the treatment of NVP. The current formulation is sugar coated and suffers from drawbacks, one of which being its delayed onset of action. However, the current formulation once ingested, can take more than 4 hours before the two active ingredients (pyridoxine HCl and doxylamine succinate) reach nearly full dissolution in the small intestines, where it is absorbed. This delay is often considered too long for patients, such as women suffering from NVP, who require urgent relief of symptoms.

Another drawback of the current formulation is related to patient compliance. Women suffering from NVP often complain of hyper olfaction, which means that various odors and tastes can trigger nausea or vomiting problems. The smell and taste of sugar on the current sugar coated formulation as well as the use of organic solvents and phthalates in the preparation of the currently used enteric coating, bothers many pregnant women to the point where the intake of the drug is essentially inhibited.

The size of the currently available tablet is also problematic. A smaller size tablet would improve patient compliance since women suffering from NVP often have problems swallowing. Furthermore, a smaller tablet looks less harmful than a bigger one and patients will have the impression that they are taking a lesser amount of drug. This will in turn significantly increase patient compliance.

Finally, the current formulation contains lactose. This is objectionable for those patients suffering from lactose intolerance.

Thus, it is desirable to provide patients suffering from nausea and vomiting an improved rapid onset formulation overcoming the drawbacks of the prior art.

However, since DS-P is orally delivered as an enteric coated tablet, the novel oral formulation must transit through the stomach unscathed and rapidly release both active ingredients once the dosage form reaches its intended destination, namely the intestines.

The main challenge surmounted by the present invention was to arrive at a dosage form capable of overcoming the drawbacks of the prior art while simultaneously delivering the synergistic duo of active ingredients for rapid onset. It was also important to provide a formulation exhibiting similar dissolution curves for both active ingredients so as to avoid the dissolution of one active ingredient to the detriment of the other. This was important in view of the synergistic therapeutic effect of the duo of active ingredients.

SUMMARY OF THE INVENTION

In general terms, the invention provides a new aqueous enteric-coated formulation comprising DS-P, the formulation exhibiting a dissolution profile indicative of a rapid onset.

The invention also seeks to provide a pharmaceutical composition having specific in-vitro dissolution profiles indicative of rapid onset of the active ingredients. The pharmaceutical composition being suitable for simple and reproducible manufacture.

Further scope of applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

DETAILED DESCRIPTION OF THE INVENTION

Figure 1:
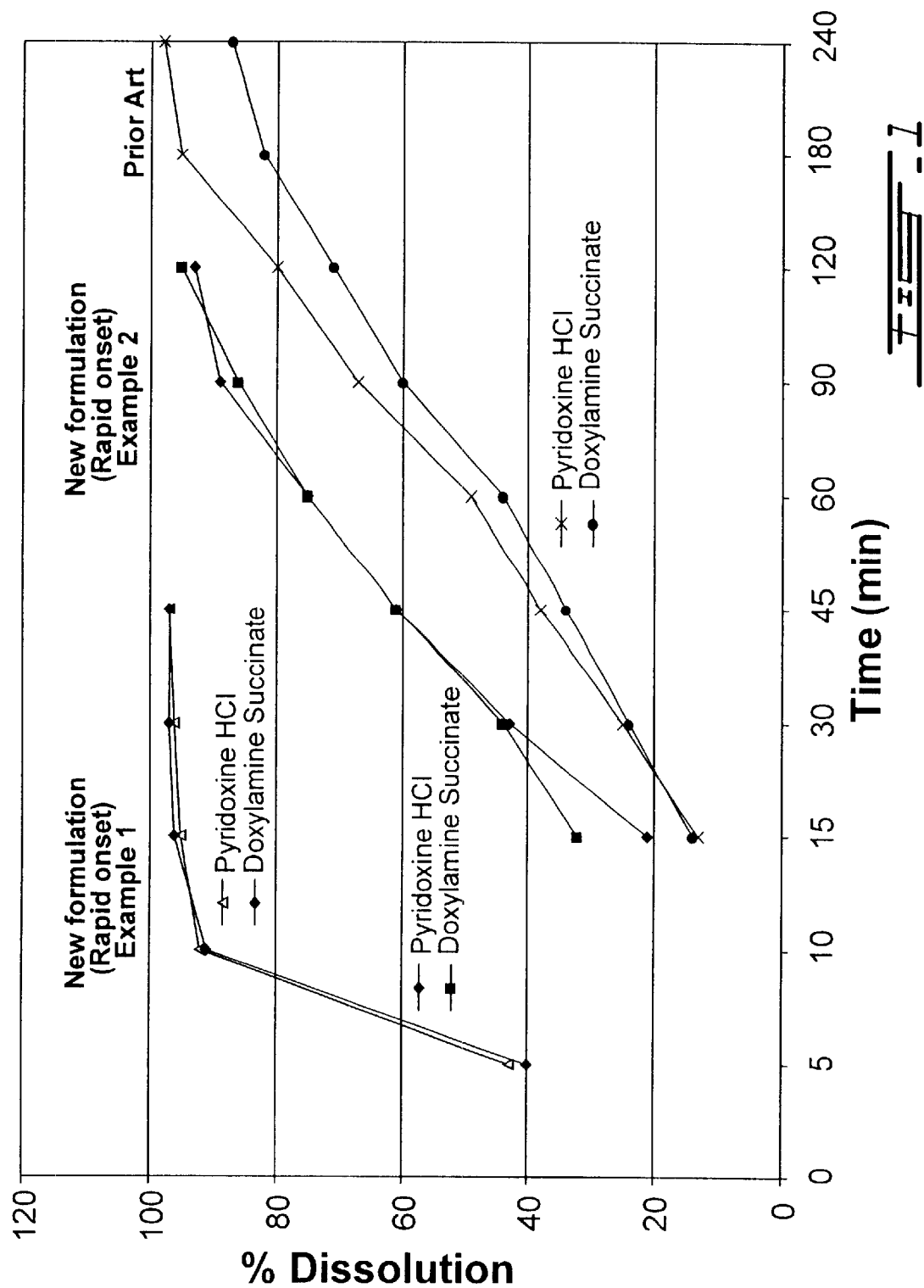
FIG. 1 depicts two examples of dissolution profiles in accordance to the rapid onset formulation of the present invention in comparison to a dissolution profile of the prior art formulation. The first dissolution profile (example 1) corresponds to a rapid onset formulation from which nearly 100% of both active ingredients is released within 45 minutes. The second dissolution profile (example 2) corresponds to a rapid onset formulation from which approximately 95% of both active ingredients is released within 120 minutes. The last and comparative dissolution profile (prior art) corresponds to the currently available formulation from which approximately 100% of the pyridoxine HCl and approximately 90% of the doxylamine succinate is released within 240 minutes.

Other objects and attendant features of the present invention will become readily appreciated, as the same becomes better understood by reference to the following detailed description of a preferred embodiment described for the purpose of illustration.

In a broad sense, the invention provides a rapid onset formulation comprising pyridoxine HCl and doxylamine succinate.

The formulation of the present invention may be used in the human and veterinary fields of medicine whenever symptoms of nausea and/or vomiting require medical intervention. Since the formulation of the present invention is intended for medicinal purposes, then the formulation and its components should be pharmaceutically acceptable. The preferred formulation is in the form of an oral dosage form such as a tablet, pill or encapsulated beads or solution. The most preferred formulation is a tablet.

The tablet of the present invention is preferably capable of transiting through the stomach unscathed. To test this feature, the tablet of the present invention was tested to resist disintegration in simulated gastric fluid "SGF" for a minimum period of 1 hour.

In accordance with the present invention, the formulation will satisfy the following dissolution profiles when measured in 1000 ml phosphate buffer at pH 6.8 and 37° C. in a type 2 dissolution apparatus at 100 rpm; preferably measured by high performance liquid chromatography:

(a) at least about 40% of the total amounts of each of pyridoxine HCl and doxylamine succinate are dissolved after 30 minutes of measurement;

(b) at least about 70% of the total amounts of each of pyridoxine HCl and doxylamine succinate are dissolved after 60 minutes of measurement;

(c) at least about 80% of the total amounts of each of pyridoxine HCl and doxylamine succinate are dissolved after 90 minutes of measurement;

(d) at least about 90% of the total amounts of each of pyridoxine HCl and doxylamine succinate are dissolved after 120 minutes of measurement;

In the present invention, any reference to dissolution profile should be construed as referring to the results of a dissolution test in which the amount of pyridoxine HCl and of doxylamine succinate released is measured in 1000 ml phosphate buffer at pH 6.8 and 37° C. using a USP (United States Pharmacopoeia) type 2 dissolution apparatus at 100 rpm; preferably measured by high performance liquid chromatography.

As used herein and in the claims, an "enteric coating" is understood to mean a coating comprising one or more layers generally resistant to disintegration in human gastric fluids, but which will disintegrate in human intestinal fluids, as well as coatings which disintegrate very slowly in human gastric fluids, but more rapidly in human intestinal fluids. In a broad sense, "enteric coating" can encompass for example any seal coat placed on the compressed core of a tablet prior to the enteric coating per se as well as any finishing aesthetic coat placed on the enteric coating per se.

In a most preferred embodiment, the formulation of the present invention contains a core coated with an aqueous enteric coating. The core comprises the active ingredients pyridoxine HCl and doxylamine succinate along with non-active excipients such as a filler or binder, a disintegrating agent, a lubricant, a silica flow conditioner and a stabilizing agent.

Examples of fillers or binders include acacia, alginic acid, calcium phosphate (dibasic), carboxymethylcellulose, carboxymethylcellulose sodium, hydroxyethylcellulose, hydroxypropylcellulose, hydroxypropylmethylcellulose, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth, microcrystalline cellulose, starch, and zein. A most preferred filler or binder consists of microcrystalline cellulose.

Examples of disintegrating agents include alginic acid, carboxymethylcellulose, carboxymethylcellulose sodium, hydroxypropylcellulose (low substituted), microcrystalline cellulose, powdered cellulose, colloidal silicon dioxide, sodium croscarmellose, crospovidone, methylcellulose, polacrilin potassium, povidone, sodium alginate, sodium starch glycolate, starch, disodium disulfite, disodium edathamil, disodium edetate, disodiumethylenediaminetetraacetate (EDTA) crosslinked polyvinylpyrollidines, pregelatinized starch, carboxymethyl starch, sodium carboxymethyl starch, microcrystalline cellulose. A most preferred disintegrating agent consists of sodium crosscarmelose.

Examples of lubricants include calcium stearate, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL leucine. A most preferred lubricant consists of magnesium stearate.

Examples of silica flow conditioners include colloidal silicon dioxide, magnesium aluminum silicate and guar gum. A most preferred silica flow conditioner consists of silicon dioxide.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol. A most preferred stabilizing agent consists of magnesium trisilicate.

In a preferred embodiment, the core of the new rapid onset Diclectin formulation will contain approximately about 4 to 10%, most preferably about 7% by weight of pyridoxine HCl; about 4 to 10%, most preferably about 7% by weight of doxylamine succinate; about 40 to 80%, most preferably about 62% by weight of microcrystalline cellulose; about 10 to 30%, most preferably about 18% by weight of magnesium trisilicate; about 0.5 to 5%, most preferably about 1% by weight of silicon dioxide; 0.5 to 5% most preferably about 3% by weight of sodium croscarmellose and about 0.5 to 5%, most preferably about 3% by weight of magnesium stearate.

EXAMPLE 1

The following is an example of a 145 mg Diclectin rapid onset core formulation:

TABLE 1

Core Ingredients:

| Ingredients | Weight Mg/Tab. | Weight %/Tab. | Batch size 100 kg |
|---|---|---|---|
| Doxylamine Succinate | 10.0 | 6.9 | 6.897 |
| Pyridoxine HCl | 10.0 | 6.9 | 6.897 |
| Magnesium trisilicate | 26.4 | 18.2 | 18.207 |
| Microcrystalline Cellulose PH 102 | 90.0 | 62.1 | 62.069 |
| Sodium Croscarmellose Type A | 3.6 | 2.5 | 2.483 |
| Magnesium Stearate | 4.0 | 2.8 | 2.759 |
| Silicon Dioxide NF | 1.0 | 0.7 | 0.690 |
| Total: | 145.0 | 100 | 100 |

The core can then be enterically coated with an aqueous enteric coating which will allow the formulation to transit through the stomach relatively unscathed while allowing rapid dissolution in the intestines.

The coating formulation can be as follows:

TABLE 2

Coating Formulation

| Ingredients | Weight Mg/Tab. | Weight % | Batch size 100 kg |
|---|---|---|---|
| Seal Coat | | | |
| Opadry ™ Clear YS-1-7472 | 4.82 | 3.33 | 3.327 |
| Purified Water USP | | | |
| Total: | 4.82 | 3.33 | 3.33 |
| Enteric Coat | | | |
| Estacryl ™ 30D Enteric Coating Solution* | 39.58 | 27.29 | 27.294 |
| Talc USP 200 Mesh | 2.85 | 1.97 | 1.968 |
| Polyethylene Glycol 400 USP | 1.20 | 0.83 | 0.826 |
| Antifoam 1520 | 0.12 | 0.08 | 0.081 |
| Purified Water USP | | | |
| Total: | 16.04 | 30.17 | 30.17 |
| Finishing Coat | | | |
| Opadry ™ White YS-1-7003 | 1.61 | 1.11 | 1.108 |
| Purified Water USP | | | |
| Total: | 1.61 | 1.11 | 1.11 |

*Estacryl 30D Enteric Coating Solution contains 30% of solids. Therefore, the total actual enteric coating amounts to 11.07%.

Total coated tablet weight 167.47 mg.

The purpose of the seal coat is to provide a smooth surface for the enteric coating, thereby avoiding mounds, pits or crevasses wherein uneven amounts of enteric coating would be applied.

Dissolution Data

The rapid onset formulation of the previous example has exhibited in-vitro dissolution profiles as shown in Table 3 below, when measured in 1000 ml phosphate buffer at pH 6.8 and 37° C. in a type 2 dissolution apparatus at 100 rpm. The numerical values are expressed as percentages of dissolved active ingredient in relation to starting quantities.

TABLE 3

Dissolution profiles

| | Run 1 | Run 2 | Run 3 | Run 4 | Run 5 | Run 6 | Avg. |
|---|---|---|---|---|---|---|---|
| Pyridoxine HCl | | | | | | | |
| 5 minutes | 20 | 2 | 0 | 77 | 79 | 79 | 43 |
| 10 minutes | 91 | 90 | 90 | 91 | 94 | 95 | 92 |
| 15 minutes | 96 | 96 | 94 | 94 | 95 | 96 | 95 |
| 30 minutes | 95 | 98 | 96 | 95 | 98 | 96 | 96 |
| 45 minutes | 97 | 96 | 97 | 94 | 99 | 98 | 97 |
| Doxylamine Succinate | | | | | | | |
| 5 minutes | 17 | 2 | 0 | 70 | 75 | 76 | 40 |
| 10 minutes | 90 | 87 | 89 | 89 | 97 | 96 | 91 |
| 15 minutes | 98 | 97 | 96 | 92 | 98 | 97 | 96 |
| 30 minutes | 97 | 98 | 96 | 94 | 99 | 97 | 97 |
| 45 minutes | 98 | 96 | 98 | 92 | 100 | 99 | 97 |

The extremely low dissolution values obtained after 5 minutes for runs 1 to 3, can be explained by the non-disintegration of the core formulation at the 5 minute interval.

Example of method of manufacture

The formulation of the present invention was prepared using the ingredients shown in Table 1, above. Doxylamine succinate and silicon dioxide NF are pre-blended in a 2 cu. Ft. V-Blender. The resulting pre-blend is then milled through a Quadro Co Mill, Model 196S, equipped with a 40 mesh screen.

Pyridoxine HCl is also milled through a Quadro Co Mill, Model 196S, equipped with a 40 mesh screen. The milled pyridoxine HCl is then combined with the doxylamine / silicon dioxide NF pre-blend and the combined mixture blended.

Microcrystalline Cellulose is milled through a 40 mesh screen and split into two approximately equal portions. One portion is subsequently combined in a 650L Gallay Bin with the previously formed pre-blend containing both the active ingredients, followed by the addition of the second portion. The loaded material is then blended followed by the addition of magnesium trisilicate and sodium croscarmellose. The newly formed mixture is blended. The addition of magnesium stearate followed by an additional blending completes the preparation of the core formulation.

Figure 2:
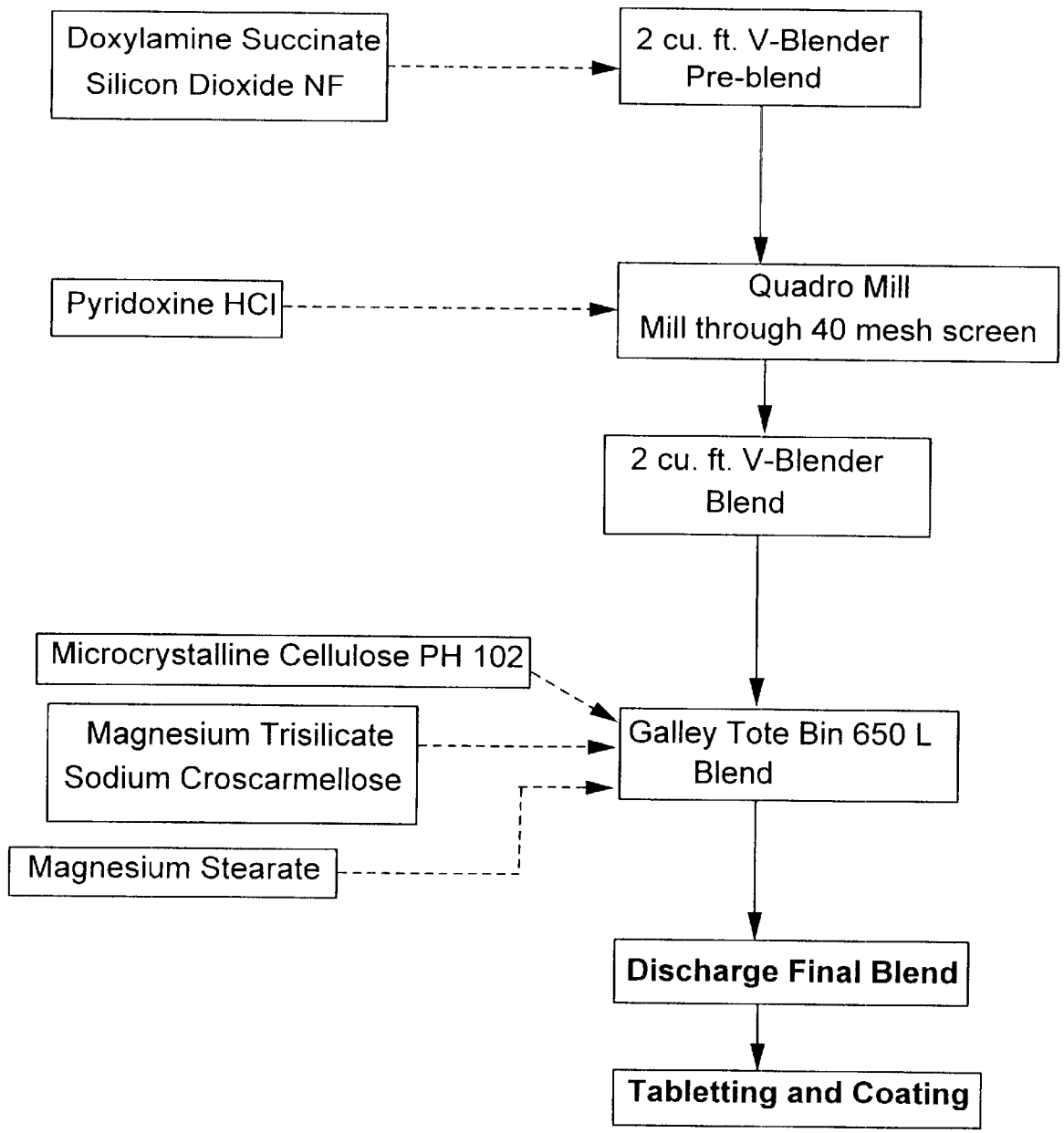
FIG. 2 is a schematic flowchart of the preferred manufacturing process of a preferred formulation in accordance with the present invention.

The final blend is compressed in tablet form and is subsequently seal coated, enteric coated using a suitable commercially available aqueous enteric coating and top coated for aesthetics. The overall manufacturing process is depicted in FIG. 2.

All coating steps using the ingredients of Table 2, namely, the seal coat on the core, the enteric coating and the opadry white (color coat) are advantageously performed in a Vector Hi (trade-mark) coater pan equipped with a peristaltic pump.

EXAMPLE 2

The following is another example of a 146 mg Diclectin rapid onset core formulation. The formulation was manufactured along the same manufacturing methods as described above in example 1. This example demonstrates that the rapid onset feature of the formulation of the present invention was obtained with a different group of excipients.

TABLE 4

Core Ingredients:

| Ingredients | Weight Mg/Tab. | Weight %/Tab. |
|---|---|---|
| Doxylamine Succinate | 10.5 | 7.2 |
| Pyridoxine HCl | 10.5 | 7.2 |
| Magnesium trisilicate | 30.0 | 20.6 |
| Microcrystalline Cellulose PH 102 | 65.0 | 44.5 |
| Calcium Phosphate (Dibasic) | 25.0 | 17.1 |
| Magnesium Stearate | 4.0 | 2.7 |
| Colloidal Silicon Dioxide | 1.0 | 0.7 |
| Total: | 146.0 | 100 |

The coating formulation can be as follows:

TABLE 5

Coating Formulation

| Ingredients | Weight/Tablet (Mg) |
|---|---|
| Opadry ™ White YS-1-7003 | 4.38 |
| Antifoam AF Emulsion | 0.07 |
| Sureteric YAE-6-18107 | 16.06 |
| Purified Water USP | |
| Opadry ™ Clear YS-1-7472 | 0.73 |

Total coated tablet weight 167.24 mg.

The rapid onset formulation of the previous example has exhibited in-vitro dissolution profiles as shown in Table 6 below, when measured in 1000 ml phosphate buffer at pH 6.8 and 37° C. in a type 2 dissolution apparatus at 100 rpm. The numerical values are expressed as percentages of dissolved active ingredient.

TABLE 6

Dissolution profiles:

|  | Run 1 | Run 2 | Run 3 | Run 4 | Run 5 | Run 6 | Avg. |
|---|---|---|---|---|---|---|---|
| Pyridoxine HCl |  |  |  |  |  |  |  |
| 15 minutes | 17 | 13 | 25 | 31 | 17 | 22 | 21 |
| 30 minutes | 31 | 28 | 60 | 63 | 36 | 43 | 43 |
| 45 minutes | 51 | 45 | 78 | 80 | 55 | 60 | 61 |
| 60 minutes | 69 | 64 | 88 | 89 | 67 | 72 | 75 |
| 75 minutes | 79 | 76 | 94 | 94 | 77 | 81 | 83 |
| 90 minutes | 84 | 84 | 97 | 97 | 83 | 87 | 89 |
| 105 minutes | 88 | 89 | 98 | 99 | 87 | 90 | 92 |
| 120 minutes | 91 | 93 | 98 | 98 | 89 | 92 | 93 |
| Doxylamine Succinate |  |  |  |  |  |  |  |
| 15 minutes | 16 | 14 | 22 | 31 | 47 | 61 | 32 |
| 30 minutes | 31 | 27 | 64 | 63 | 38 | 40 | 44 |
| 45 minutes | 47 | 44 | 75 | 79 | 58 | 61 | 61 |
| 60 minutes | 71 | 61 | 90 | 85 | 68 | 74 | 75 |
| 75 minutes | 76 | 71 | 96 | 89 | 81 | 82 | 82 |
| 90 minutes | 85 | 80 | 101 | 88 | 83 | 81 | 86 |
| 105 minutes | 92 | 86 | 103 | 95 | 93 | 92 | 93 |
| 120 minutes | 93 | 88 | 101 | 96 | 96 | 95 | 95 |

It follows from these results that the novel formulation demonstrates a rapid onset as shown by its dissolution profile. Pyridoxine HCl presents an average dissolution profile of over 90% within 120 minutes of starting the measurements. Similarly, Doxylamine succinate displays an average dissolution profile of over 90% within 120 minutes of starting the measurements.

EXAMPLE 3

(Comparative example using prior art formulation)

The following is an example of the prior art Diclectin formulation. An example for a 146.2 mg tablet is provided. This example demonstrates a strikingly slower onset of dissolution in comparison to the present invention.

TABLE 7

Core Ingredients:

| Ingredients | Weight Mg/Tab. | Weight %/Tab. |
|---|---|---|
| Pyridoxine HCl | 11.0 | 7.5 |
| Doxylamine Succinate | 10.2 | 7.0 |
| Lactose NF | 25.0 | 17.1 |
| Microcrystalline Cellulose NF | 65.0 | 44.4 |
| Magnesium Trisilicate | 30.0 | 20.6 |
| Silicon Dioxide | 1.0 | 0.7 |
| Magnesium Stearate | 4.0 | 2.7 |
| Total: | 146.2 | 100 |

The coating formulation is as follows:

TABLE 8

Coating Formulation

Ingredients

Coating Solution No. 714
Coating Powder No. 303
C.A.P. solution 10%
C.A.P. solution 5%
Gelatin Solution No. 105
Dusting Powder No. 755
White Smoothing Syrup
Sugar Syrup No. 111
Opalux AS-7000-B white
Wax Solution No. 723

The current formulation of the previous example has exhibited in-vitro dissolution profiles as shown in Table 9 below, when measured in 1000 ml phosphate buffer at pH 6.8 and 37° C. in a type 2 dissolution apparatus at 100 rpm. The numerical values are expressed as percentages of dissolved active ingredient.

TABLE 9

Dissolution profiles:

|  | Run 1 | Run 2 | Run 3 | Run 4 | Run 5 | Run 6 | Avg. |
|---|---|---|---|---|---|---|---|
| Pyridoxine HCl |  |  |  |  |  |  |  |
| 15 minutes | 9 | 11 | 18 | 11 | 16 | 12 | 13 |
| 30 minutes | 22 | 23 | 32 | 25 | 28 | 23 | 25 |
| 45 minutes | 37 | 34 | 45 | 39 | 42 | 34 | 38 |
| 60 minutes | 50 | 44 | 56 | 49 | 51 | 44 | 49 |
| 90 minutes | 69 | 63 | 73 | 69 | 67 | 63 | 67 |
| 120 minutes | 83 | 76 | 84 | 82 | 80 | 76 | 80 |
| 150 minutes | 94 | 86 | 91 | 91 | 86 | 86 | 89 |
| 180 minutes | 99 | 94 | 98 | 96 | 93 | 92 | 95 |
| 240 minutes | 93 | 93 | 100 | 100 | 99 | 101 | 98 |
| Doxylamine Succinate |  |  |  |  |  |  |  |
| 15 minutes | 12 | 15 | 17 | 8 | 18 | 16 | 14 |
| 30 minutes | 17 | 21 | 31 | 18 | 27 | 30 | 24 |
| 45 minutes | 24 | 32 | 45 | 25 | 38 | 38 | 34 |
| 60 minutes | 34 | 41 | 56 | 36 | 46 | 49 | 44 |
| 90 minutes | 52 | 55 | 69 | 55 | 62 | 66 | 60 |
| 120 minutes | 69 | 65 | 75 | 68 | 71 | 75 | 71 |
| 150 minutes | 80 | 74 | 80 | 78 | 79 | 82 | 79 |
| 180 minutes | 82 | 78 | 86 | 82 | 80 | 84 | 82 |
| 240 minutes | 95 | 89 | 89 | 82 | 80 | 87 | 87 |

It follows from these results that the prior art formulation, exhibits a noticeably slower dissolution pattern when compared with the novel formulations. Indeed, after 90 minutes averages of only 60% doxylamine and 67% pyridoxine HCl are dissolved. A slower in-vivo dissolution profile is indicative of a delayed onset of action. The novel formulations, as depicted by examples 1 and 2, show markedly faster onset dissolution profiles resulting in a rapid onset of action. The new formulations overcome most, if not all of the drawbacks associated with the prior art.

The terms and descriptions used herein are preferred embodiments set forth by way of illustration only, and are not intended as limitations on the many variations which those of skill in the art will recognize to be possible in practicing the present invention. It is the intention that all variants whether presently known or unknown, that do not have a direct effect upon the way the invention works, are to be covered by the following claims.

What is claimed is:

1. An enterically-coated pyridoxine HCl and doxylamine succinate rapid onset formulation comprising a disintegrating agent such that the following dissolution profiles are satisfied when measured in 1000 ml phosphate buffer at pH 6.8 and 37° C. in a type 2 dissolution apparatus at 100 rpm:

(a) at least about 40% of the total amounts of each of pyridoxine HCl and doxylamine succinate are dissolved after 30 minutes of measurement;

(b) at least about 70% of the total amounts of each of pyridoxine HCl and doxylamine succinate are dissolved after 60 minutes of measurement;

(c) at least about 80% of the total amounts of each of pyridoxine HCl and doxylamine succinate are dissolved after 90 minutes of measurement;

(d) at least about 90% of the total amounts of each of pyridoxine HCl and doxylamine succinate are dissolved after 120 minutes of measurement.

2. An enterically-coated pyridoxine HCl and doxylamine succinate rapid onset formulation as in claim 1, wherein the following dissolution characteristics are also satisfied when measured in 1000 ml phosphate buffer at pH 6.8 and 37° C. in a type 2 dissolution apparatus at 100 rpm:

(a) at least about 20% of the total amounts of each of pyridoxine HCl and doxylamine succinate are dissolved after 15 minutes of measurement;

(b) at least about 60% of the total amounts of each of pyridoxine HCl and doxylamine succinate are dissolved after 45 minutes of measurement;

(c) at least about 80% of the total amounts of each of pyridoxine HCl and doxylamine succinate are dissolved after 75 minutes of measurement.

3. The rapid onset formulation of claim 1, wherein at least about 40% of the total amounts of each of pyridoxine HCl and doxylamine succinate are dissolved within 5 minutes when measured in 1000 ml phosphate buffer at pH 6.8 and 37° C. in a type 2 dissolution apparatus at 100 rpm.

4. The rapid onset formulation of claim 2, wherein at least about 40% of the total amounts of each of pyridoxine HCl and doxylamine succinate are dissolved within 5 minutes when measured in 1000 ml phosphate buffer at pH 6.8 and 37° C. in a type 2 dissolution apparatus at 100 rpm.

5. The rapid onset formulation of claim 1, wherein said formulation contains a core coated with at least one enteric coating, said core comprising pyridoxine HCl, doxylamine succinate and the following non-active excipients: a filler or binder, a disintegrating agent, a lubricant, a silica flow conditioner and a stabilizing agent.

6. The rapid onset formulation of claim 2, wherein said formulation contains a core coated with at least one enteric coating, said core comprising pyridoxine HCl, doxylamine succinate and the following non-active excipients: a filler or binder, a disintegrating agent, a lubricant, a silica flow conditioner and a stabilizing agent.

7. The rapid onset formulation of claim 5, wherein said filler or binder consists of microcrystalline cellulose.

8. The rapid onset formulation of claim 6, wherein said filler or binder consists of microcrystalline cellulose.

9. The rapid onset formulation of claim 5, wherein said disintegrating agent consists of sodium crosscarmellose.

10. The rapid onset formulation of claim 6, wherein said disintegrating agent consists of sodium crosscarmellose.

11. The rapid onset formulation of claim 5, wherein said lubricant consists of magnesium stearate.

12. The rapid onset formulation of claim 6, wherein said lubricant consists of magnesium stearate.

13. The rapid onset formulation of claim 5, wherein said silica flow conditioner consists of silicon dioxide.

14. The rapid onset formulation of claim 6, wherein said silica flow conditioner consists of silicon dioxide.

15. The rapid onset formulation of claim 5, wherein said stabilizing agent consists of magnesium trisilicate.

16. The rapid onset formulation of claim 6, wherein said stabilizing agent consists of magnesium trisilicate.

17. The rapid onset formulation of claim 1, wherein said core comprises:

(a) about 4–10% by weight of pyridoxine HCl;

(b) about 4–10% by weight of doxylamine succinate;

(c) about 40–80% by weight of microcrystalline cellulose;

(d) about 10–30% by weight of magnesium trisilicate;

(e) about 0.5–5% by weight of silicon dioxide;

(f) about 0.5–5% by weight of sodium croscarmellose; and (g) about 0.5–5% by weight of magnesium stearate.

18. The rapid onset formulation of claim 2, wherein said core comprises:

(a) about 4–10% by weight of pyridoxine HCl;

(b) about 4–10% by weight of doxylamine succinate;

(c) about 40–80% by weight of microcrystalline cellulose;

(d) about 10–30% by weight of magnesium trisilicate;

(e) about 0.5–5% by weight of silicon dioxide;

(f) about 0.5–5% by weight of sodium croscarmellose; and (g) about 0.5–5% by weight of magnesium stearate.

19. The rapid onset formulation of claim 17, wherein said core comprises:

(a) about 7% by weight of pyridoxine HCl;

(b) about 7% by weight of doxylamine succinate;

(c) about 62% by weight of microcrystalline cellulose;

(d) about 18% by weight of magnesium trisilicate;

(e) about 1% by weight of silicon dioxide;

(f) about 3% by weight of sodium croscarmellose; and (g) about 3% by weight of magnesium stearate.

20. The rapid onset formulation of claim 18, wherein said core comprises:

(a) about 7% by weight of pyridoxine HCl;

(b) about 7% by weight of doxylamine succinate;

(c) about 62% by weight of microcrystalline cellulose;

(d) about 18% by weight of magnesium trisilicate;

(e) about 1% by weight of silicon dioxide;

(f) about 3% by weight of sodium croscarmellose; and (g) about 3% by weight of magnesium stearate.

21. The rapid onset formulation of claim 5, wherein said enteric coating(s) is (are) aqueous based.

22. The rapid onset formulation of claim 6, wherein said enteric coating(s) is (are) aqueous based.

23. The rapid onset formulation of claim 21, wherein said enteric coating consists of a seal coat applied to the core, an enteric coating per se applied on the seal coat and an aesthetic top coat applied on the enteric coating per se.

24. The rapid onset formulation of claim 22, wherein said enteric coating consists of a seal coat applied to the core, an enteric coating per se applied on the seal coat and an aesthetic top coat applied on the enteric coating per se.

25. A method of treating nausea and vomiting comprising administering a therapeutically effective amount of the rapid onset formulation of claim 1 to a patient in need thereof.

26. A method of treating nausea and vomiting comprising administering a therapeutically effective amount of the rapid onset formulation of claim 2 to a patient in need thereof.

27. A method of treating nausea and vomiting during pregnancy comprising administering a therapeutically effective amount of the rapid onset formulation of claim 1.

28. A method of treating nausea and vomiting during pregnancy comprising administering a therapeutically effective amount of the rapid onset formulation of claim 2.

29. A medicament for attenuating the symptoms associated with nausea and vomiting consisting essentially of the formulation of claim 5.

30. A medicament for attenuating the symptoms associated with nausea and vomiting consisting essentially of the formulation of claim 6.

* * * * *